United States Patent [19]
Koester et al.

[11] Patent Number: 5,089,022
[45] Date of Patent: Feb. 18, 1992

[54] RECTIFIED INTRAOCULAR LENS

[75] Inventors: Charles J. Koester, Glen Rock, N.J.; James D. Auran, New York, N.Y.

[73] Assignee: The Trustees of Columbia University in the City of New York, New York, N.Y.

[21] Appl. No.: 344,099

[22] Filed: Apr. 26, 1989

[51] Int. Cl.$^5$ .............................. A61F 2/16
[52] U.S. Cl. ............................................ 623/6
[58] Field of Search ............................. 623/6

[56] References Cited

U.S. PATENT DOCUMENTS

| | | | |
|---|---|---|---|
| 4,253,200 | 3/1981 | Kelman | 623/6 |
| 4,441,217 | 4/1984 | Cozean, Jr. | 623/6 |
| 4,648,878 | 3/1987 | Kelman | 623/6 |

Primary Examiner—Ronald Frinks
Attorney, Agent, or Firm—John P. White

[57] ABSTRACT

An intraocular lens exhibits handedness and comprises a refractive portion and haptics extending out from the refractive portion. The lens is designed to minimize errors in centration and tilt that are statistically different in the case of implantation in right and left eyes, respectively. The haptics and/or the refractive portion of the lens is radially asymmetric in such a manner that, except for structural characteristics attributable to refractive prescription, a lens intended for implantation in a left eye is a mirror image of a lens intended for implantation in a right eye. The haptics engage the eye in any manner desired by the surgeon, and the design is such that the optical zone of the refractive portion is then centered on the pupil and the optical axis of the refractive portion coincides with, or has some other prescribed relation to, the visual axis of the eye.

19 Claims, 5 Drawing Sheets

RECTIFIED INTRAOCULAR LENS

BACKGROUND OF THE INVENTION

This invention relates to lenses for implantation in aphakic eyes and, more particularly, to a novel and highly-effective intraocular lens that makes it possible to correct for errors in centration and tilt that have now been found to be statistically different in the case of conventional implantation in right and left eyes, respectively. The invention relates also to a method by which normal vision can be more nearly restored to aphakic eyes.

Surgical removal of the crystalline lens of the eye because of various medical problems including notably the development of cataracts has become commonplace. The crystalline lens is replaced with an intraocular lens (IOL) equipped with haptics for maintaining the IOL in a predetermined position in the eye. Various mounting locations for the IOL have been proposed, including the anterior and posterior chambers, and within each chamber various placements of the haptics have been proposed. For example in the case of an IOL implanted in the posterior chamber, both haptics can engage the ciliary sulcus or the capsular bag (symmetric fixation) or one haptic can engage the ciliary sulcus and the other the capsular bag (asymmetric fixation).

A U.S. Pat. No. 4,235,200 to Kelman discloses various examples of IOLs designed to compensate for the tilting of the lens that otherwise occurs when one haptic, for example the superior haptic, engages the ciliary sulcus and the other (inferior) haptic engages the capsular bag. In accordance with the teaching of the patent, one of the haptics is provided with a portion that is either stepped or angled in order to eliminate the tilt that would otherwise result from the asymmetric fixation of the haptics. Also, the haptic engaging the ciliary suclus is either longer or less flexible than the haptic engaging the capsular bag in order to compensate for the decentration that would otherwise result from the asymmetric fixation.

In accordance with this and other teachings of the prior art, however, as exemplified by U.S. Pat. Nos. 2,834,023, 4,087,866, 4,316,292, 4,327,450, 4,328,595, 4,441,217, 4,535,488, 4,601,721, 4,657,546, 4,657,547, 4,704,123, 4,718,904, and 4,734,095 and Phillips, P. et al., Measurement of intraocular lens decentration and tilt in vivo, J. Cataract Refract. Surg. 14:129–135, 1988, decentration and tilt, to the extend that they are recognized as problems at all, are considered to be independent of the "handedness" of the eye in which the IOL is implanted, and an IOL intended for implantation in the OD (oculus dexter or right eye) is no different, except of course for the refractive correction, from an IOL intended for implantation in the OS (oculus sinister or left eye).

Is now been found through careful measurements made on scores of patients with implanted IOLs that there is a systematic, statistically significant difference between the errors in centration and tilt that accompany implantations of IOLs in left eyes and those that accompany implantations of IOLs in right eyes.

Specifically, measurement of posterior chamber intraocular lenses, all implanted by the same surgeon, in a series of 103 eyes has shown that lenses tend to decenter superotemporally and to tilt with the superonasal edges tipped forward. Decentration induces prism and other optical aberrations and can result in exposure of edges and positioning holes within the pupil. Average decentration in the 103 eyes was 0.68 millimeters. Tilt produces astigmatism and coma that increases with the square of the tilt angle. Average tilt was 6.6°, an amount that produces less than 0.25 diopters of astigmatism. By comparison, 15° of tilt produces one diopter of astigmatism.

It is generally considered advisable to center the intraocular lens on the pupil. The intraocular lens is conventionally radially symmetrical so that if the lens is centered on the pupil the optical center of the lens is on the line of sight of the aphakic eye. Such placement of an intraocular lens does not optimally restore the optical alignment of an aphakic eye if, as is often the case, the visual axis of the aphakic eye is not coincident with the line of sight. Moreover, the surgeon cannot accurately judge where the center of the pupil (or line of sight) is, especially since the center of the pupil often migrates slightly when the pupil is pharmacologically dilated in preparation for surgery.

SUMMARY OF THE INVENTION

An object of the invention is to remedy the problems of the prior art noted above and, in particular, to provide an intraocular lens that makes it possible to correct for errors in centration and tilt that are consistent from patient to patient, or that can be predicted from pre-operative measurements of the individual eye, and that are statistically different in the case of implantation in right and left eyes, respectively. For example, it has now been found that axial length of the eye (distance from the corneal apex to the fovea) correlates with decentration and tilt magnitude: Increased axial length is associated with increased decentration and reduced tilt. Thus the haptic/optic design may be altered according to the axial length of the eye.

Another object of the invention is to provide an intraocular lens that can be positioned for optimum restoration of the visual acuity of an aphakic eye without exposing an edge of the lens through the pupil.

The foregoing and other objects are achieved in accordance with a first aspect of the invention by the provision of an intraocular lens for mounting in an aphakic eye, the lens having refractive means defining an optical zone and haptic means extending out from the refractive means, the refractive means and haptic means having a combined structure that exhibits handedness, whereby, when the haptic means engages the eye in a predetermined manner, ocular characteristics that affect the position of the lens in the eye and that are statistically different in the case of implantation in right and left eyes, respectively, are compensated for so that the optical zone is centered on the pupil.

In accordance with another aspect of the invention, there is provided an intraocular lens for mounting in an aphakic eye having a line of sight, the intraocular lens having refractive means defining an optical zone and haptic means extending out from the refractive means, the refractive means and haptic means forming a combined structure that exhibits handedness, whereby, when the haptic means engages the eye in a predetermined manner, ocular characteristics that affect the tilt of the lens in the eye and that are statistically different in the case of implantation in right and left eyes, respectively, are compensated for so that the tilt of the lens can be made to assume any predetermined value relative to the line of sight.

In accordance with an independent aspect of the invention, an intraocular lens is provided for mounting at a given lens mounting location in an aphakic eye having a pupil, a line of sight and a visual axis which at a given lens mounting location in the eye is displaced from the line of sight by a given distance, the lens comprising (i) refractive means having an optical axis, an optical center, an optical zone and an optical zone center displaced from the optical center a distance having a predetermined relation to said given distance and (ii) haptic means extending out from the refractive means and being so related to the refractive means that when the haptic means engages the eye in a predetermined manner at said given lens mounting location the optical zone is centered on the pupil and the optical and visual axes have a prescribed relation with respect to each other. For example, the optical center may lie on the visual axis, thereby compensating for decentration, or the optical axis may be parallel to the visual axis, thereby compensating for tilt. In one preferred embodiment, the optical center is on the visual axis and the optical axis is parallel to the visual axis—in other words, the optical and visual axes coincide—, thereby compensating for both decentration and tilt.

In accordance with an independent aspect of the invention there is provided an intraocular lens exhibiting handedness and comprising refractive means and haptic means extending out from the refractive means, the lens being designed to compensate for ocular characteristics that affect centration or tilt and that are statistically different in the case of implantation in right and left eyes, respectively, the intraocular lens being radially asymmetric in such a manner that, except for structural characteristics attributable to refractive prescription, a lens intended for implantation in a left eye is a mirror image of a lens intended for implantation in a right eye.

In accordance with another independent aspect of the invention, an intraocular lens is provided for placement in an aphakic eye having a pupil and a visual axis, the lens being formed with refractive means defining an optical axis, an optical center, and an optical zone and with haptic means extending out from the refractive means for positioning the lens in the eye, the refractive means and the haptic means being formed relative to each other so that the lens can be mounted in the eye with a predetermined azimuth such that the optical zone is centered on the pupil and the optical and visual axes have a prescribed relation with respect to each other.

In accordance with a further independent aspect of the invention, there is provided a method of improving vision of an aphakic eye having a pupil, a line of sight and a measurement axis which at a given lens mounting location in the eye is displaced from the line of sight by a given distance, the method comprising the steps of mounting at said mounting location an intraocular lens formed with (i) refractive means having an optical center, an optical zone and an optical zone center displaced from the optical center by a distance having a predetermined relation to said given distance and (ii) haptic means extending out from the refractive means and being so related to the refractive means that when the haptic means engages the eye in a predetermined manner for mounting the lens at said given lens mounting location the optical and measurement axes have a prescribed relation with respect to each other and the optical zone is centered on the pupil.

In accordance with a further independent aspect of the invention, there is provided a method of improving vision of an aphakic eye, the eye having a pupil and the method comprising the steps of inserting in the eye an intraocular lens formed with refractive means of a suitable dioptric power and having an optical axis, an optical zone center, and a pair of asymmetric haptics, the optical axis being displaced from the optical zone center and the haptics being arranged along a haptic axis, and engaging the haptics with the ocular structure, thereby establishing symmetric haptic fixation, the haptic axis being oriented so that the optical zone is substantially centered on the pupil and the displacement and orientation of the optical axis and the optical zone center relative to each other compensates for at least one of (i) decentration and (ii) tilt induced along any predetermined meridian relative to the haptic axis.

In accordance with a further independent aspect of the invention, there is provided a method of implanting, in an aphakic eye having a visual axis and a pupil having a center displaced from the visual axis, an intraocular lens having haptic means, an optical axis, an optical center and an optical zone, the method comprising the steps of orienting the intraocular lens to a predetermined azimuth and engaging the haptic means with predetermined ocular structure, the visual axis then being parallel to the optical axis or intersecting the optical center and the optical zone being concentric with the pupil.

In accordance with another independent aspect of the present invention, there is provided a method of implanting in an aphakic eye having a visual axis and a pupil having a center displaced from the visual axis, an intraocular lens having haptic means and an optical axis, the method comprising the steps of engaging the haptic means with predetermined ocular structure, the haptic means being oriented along an azimuth such that the optical axis is coincident with the visual axis of the aphakic eye.

Other objects, features and advantages of the invention may be better understood from a consideration of the following detailed description of the preferred embodiments thereof, in conjunction with the appended figures of the drawing.

DETAILED DESCRIPTION OF THE INVENTION

Figure 1:
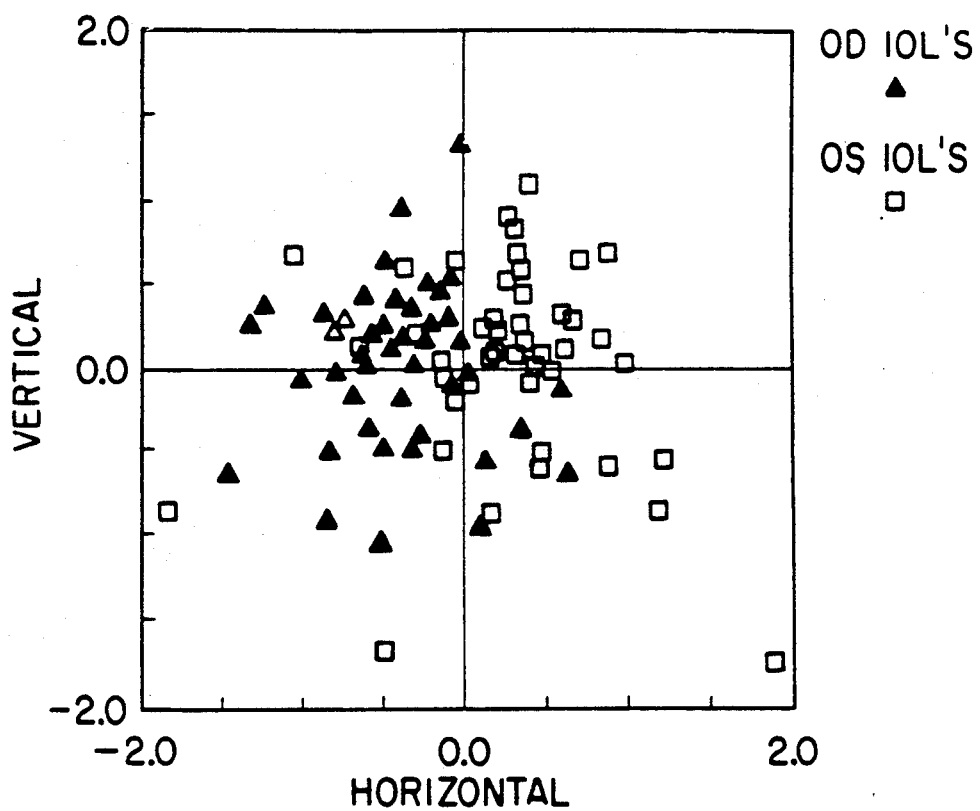
FIG. 1 is a scatter plot showing the decentration of 103 intraocular lenses in the coronal plane relative to the cornea light reflex axis (measurement axis), in millimeters, wherein solid triangles show decentration in right eyes and open squares show decentration in left eyes.

The following definitions are understood by those skilled in the art and will assist others to understand the invention:

Cornea: The transparent part of the coat of the eyeball that covers the iris and pupil and admits light to the interior.

Cornea light reflex axis: Measurement axis (qv).

Coronal plane: A vertical plane normal to the sagittal plane.

Fovea: The small rodless area of the retina affording acute vision.

Haptic: A structure, usually one of two, connected to the refractive portion of an IOL and adapted to engage an ocular structure in order to mount the IOL in the eye.

Iris: The opaque contractile diaphragm that defines the pupil.

Lambda: The angle between the pupillary axis and the line of sight.

Line of sight: A line passing from the fixation point through the center of the pupil.

Measurement axis: A line parallel to the line of the sight and perpendicular to the cornea; also known as the cornea light reflex axis. In the aphakic eye, this is the same as the visual axis and optical axis of the eye. In the pseudophakic eye, it is parallel to the line of sight and visual axis outside the eye.

Crystalline lens: The natural lens of the eye.

Nodal points: First and second points such that a light ray coming from outside the system, directed toward the first point, will appear to emerge from the second point and travel in a straight line to the image along a line parallel to its initial direction.

Optic: Optical zone (qv).

Optical axis (of IOL): The line that passes through the centers of the curvature of the lens surfaces. If one surface is plane, the optical axis is the line that passes through the center of curvature of the curved surface and is perpendicular to the plane surface.

Optical center: The intersection of the optical axis with the lens.

Optical zone: The refractive portion of an intraocular lens; also known as the optic of the IOL.

Pupillary axis: A line perpendicular to the cornea and passing through the center of the pupil.

Sagittal plane: The median plane of the body.

Symmetric (as applied to haptic fixation): Engaging the same ocular structure (e.g., ciliary sulcus or capsular bag).

Symmetric (as applied to haptics): Having the same size, shape and construction.

Visual axis (of aphakic eye): A line passing through the fovea and the fixation point (this line passes also through the center of curvature of the cornea). The visual axis, rather than, for example, the line of sight, is the true optical axis of the eye. However, because of the difficulty of measuring the visual axis directly in the normal or pseudophakic eye, the measurement axis or line of sight is used clinically.

Visual axis (of normal or pseudophakic eye): A broken line passing from the fixation point through the first and second nodal points to the fovea.

It has been found that, when a single surgeon implants a single type of intraocular lens in the posterior chamber, there is a definite pattern to the decentrations and tilts, in that they tend to follow supporting anatomical structures in the eye. That is, the intraocular lens tends to be more nearly centered on the ciliary body and sulcus, zonules and lens capsule than on the pupil or the optics of the eye; and the tilt of the IOL tends to be in the direction of the tilt of the crystalline lens.

In accordance with the present invention, the optical portion of the lens is preferably decentered and/or tilted with respect to the supporting haptic structure as described below.

FIG. 1 is a scatter plot showing the decentration of 103 intraocular lenses in the coronal plane relative to the cornea light reflex axis or visual axis, in millimeters (wherein solid triangles show decentration in right eye and open squares show decentration in left eyes). The scatter plot of FIG. 1 makes it very evident that there is a systematic variation in the decentration of intraocular lenses implanted in right and left eyes, respectively.

Figure 2:
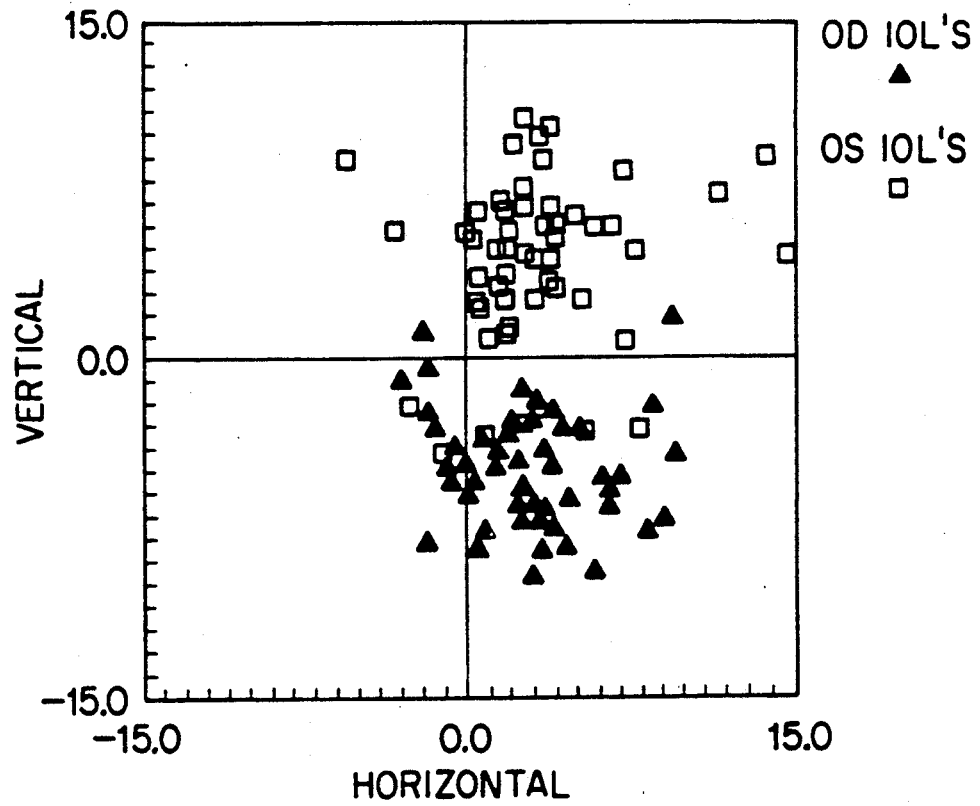
FIG. 2 is a scatter plot showing the tilt of 103 intraocular lenses in the coronal plane relative to the cornea light reflex axis (measurement axis), in degrees, wherein solid triangles show tilt in right eyes and open squares show tilt in left eyes.

FIG. 2 is a scatter plot showing the tilt of 103 intraocular lenses relative to the cornea light reflex axis or visual axis, in degrees (solid triangles represent right eyes and open squares left eyes). In FIG. 2, a positive X-axis value implies that the superior aspect of the lens is anterior while a negative X-axis value implies that the superior aspect of the lens is posterior. A positive Y-axis value implies that the aspect of the lens to the observer's left is anterior, while a negative X-axis value implies that the aspect of the lens to the observer's left is posterior. The scatter plot of FIG. 2 makes it very evident that there is a systematic variation in the tilt of intraocular lenses implanted in right and left eyes, respectively. The invention is adapted especially to compensate for the systematic errors in centration and tilt (FIGS. 1 and 2) of intraocular lenses implanted in accordance with the current state of the art in right and left eyes, respectively. As FIG. 1 shows, a majority of intraocular lenses are decentered superotemporally, the average intraocular lens decentration being about 0.349 (right eye) or 0.29 (left eye) millimeters superotemporal to the cornea light reflex axis. The difference in decentration direction between right and left eyes is highly significant (in a statistical t test, p is less than 0.001). In 103 lenses measured in the series, the average magnitude of decentration, regardless of direction, was 0.68 millimeters. The average magnitude of intraocular lens decentration was 0.62 millimeters relative to the cornea light reflex axis and 0.63 millimeters relative to the line of sight.

Intraocular lens tilt azimuth is measured with respect to the axis about which the intraocular lens is rotated relative to the plane perpendicular to the line of sight (in front of the eye). The azimuth is an angle measured counterclockwise from (i) a reference line extending horizontally to the right from a point of origin to (ii) a second line (in this case the axis about which the IOL is rotated) passing through the point of origin. From the examiner's viewpoint, the pole of the intraocular lens tilting forward (displaced anteriorly) is at 90° plus the azimuth of tilt. For example, with a tilt azimuth of 30°, the anterior-leaning pole of the intraocular lens is at 120° and the posterior-leaning (posteriorly displaced) pole is at $-60°$ (300°). Tilt magnitude for the 103 eyes averaged 6.60 with lenses tending to tilt with their superonasal edges tipped forward. The difference in tilt azimuths between right and left eyes is highly significant (p is less than 0.001).

Intraocular lens position within the eye can in principle be measured in vivo directly relative to fixed anatomical structures (e.g., the ciliary body), the optical axis of the eye, or the line of sight.

The image-forming light bundle is defined by the pupil, and the line of sight represents the central ray in the image-forming bundle. However, the center of the pupil is not a fixed reference point; it can change with pupil dilation and with time. The pupil is not necessarily centered on the visual axis, and an intraocular lens centered on a decentered pupil will induce prism.

For the aphakic eye, the visual axis is the true optical axis of the eye. If an implanted intraocular lens is centered relative to this axis, that intraocular lens will be recorded as having zero decentration. If the IOL is not centered relative to this axis, its decentration is defined relative to either the measurement axis or the line of sight.

As explained above, there is a bilaterally symmetric tendency for posterior chamber intraocular lenses to lie temporal and slightly superior to both the cornea light reflex axis (measurement axis) and the line of sight. There are several possible explanations for the observed decentration. (1) Part of the decentration may sometimes be explained by asymmetric haptic fixation. With one haptic in the capsular bag and one in the ciliary sulcus, decentration in the direction of the haptic in the ciliary sulcus results unless the haptics are given a compensating asymmetry. (2) It has been observed that the average decentration in the study referred to above is approximately 180° from the inferonasal meridian of closure of the fetal tissue. (3) It may also be true that the crystalline lens is decentered superotemporal to the line of sight and visual axis. (4) Moreover, operative technique may be a factor. A consistent pattern of variation in the completeness of lens cortical cleanup at different meridians of the capsular bag could result in asymmetric capsular fibrosis, causing intraocular lens decentration in one direction.

From an optical point of view the best position for the optical center of the IOL is on the visual axis of the aphakic eye. In this case there will be no induced prism, and no alterations due to decentration of the IOL relative to the cornea. However, there are other considerations that may make another position preferable in certain patients. For instance, it should be noted that the natural lens is decentered superiorly. Therefore, a certain induced prism is produced by the natural lens. When the crystalline lens is replaced by an IOL, it may be desired to duplicate the prism effect of the natural lens, in some cases. This would be particularly so in a case where the patient is expected to have trouble adapting to a prism effect in the operated eye (older patients, patients with pre-existing strabismus, and patients with cerebellar dysfunction). In most cases the patient would have no difficulty adapting to the small amount of change in prism caused by a centered IOL. In other cases it may be desired to deliberately introduce a predetermined degree of prism power, for therapeutic purposes. An example would be a strabismus patient where prism power is needed so that the patient can achieve binocular vision.

Figure 3:
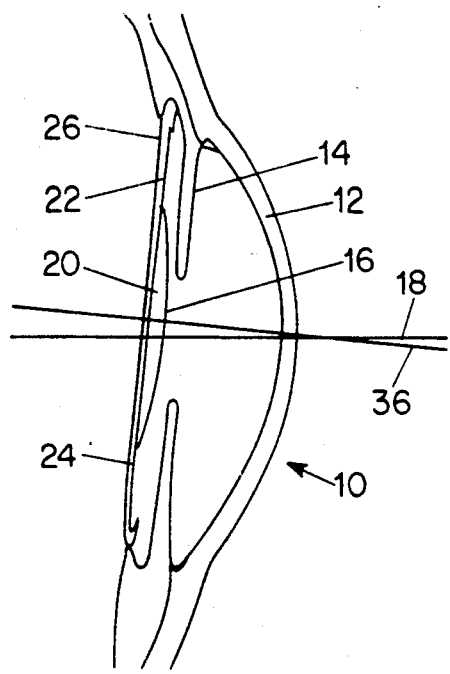
FIG. 3 is a fragmentary sectional view of an aphakic eye in a vertical plane containing the line of sight of the eye and showing the decentration resulting from the implantation therein with symmetric fixation of a conventional intraocular lens having symmetric haptics.

FIG. 3 is a fragmentary sectional view of an aphakic eye 10 having a cornea 12, iris 14, pupil 16 and line of sight 18. The line of sight lB is defined by the fovea (not shown in FIG. 1) and the center of the pupil 16. A conventional intraocular lens 20 is implanted in the eye 10. The intraocular lens 20 has symmetric haptics including a superior haptic 22 and an inferior haptic 24. The fixation of the haptics 22, 24 is symmetric: i.e., each haptic 22, 24 engages the same ocular structure, in this case the capsular bag 26.

Figure 4:
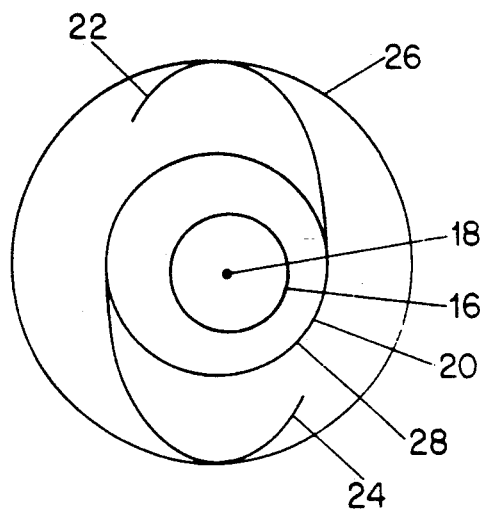
FIG. 4 is a view in front elevation of the structure of FIG. 3.

As FIG. 4 shows, this results in decentration of the intraocular lens 20 relative to the pupil 16. As a result, an edge 28 of the lens 20 may be visible through the pupil 16 when the pupil 16 dilates. This is cosmetically objectionable and moreover degrades the vision of the wearer of the lens 20, since some of the light passing through the pupil 16 will bypass the lens 20 and impinge on the retina (not shown) in an unfocused state and glare is likely to be produced by the light that impinges on the lens 20 very close to the edge 28 thereof.

Figure 5:
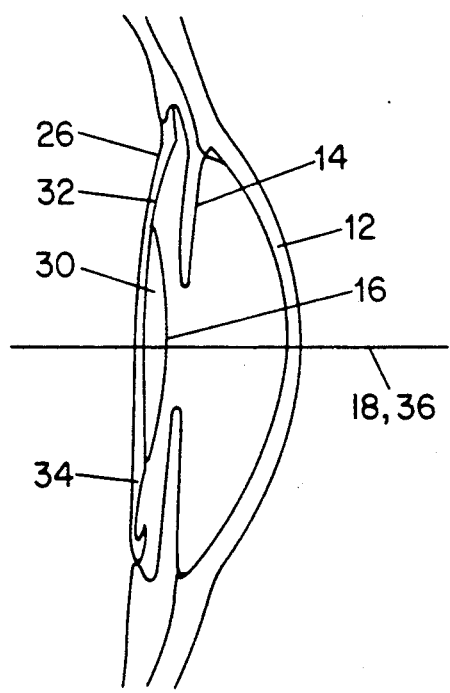
FIG. 5 is a fragmentary sectional view of an aphakic eye in a vertical plane containing the line of sight of the eye and showing the correct centration and tilt resulting from the implantation therein with symmetric fixation of one embodiment of an intraocular lens constructed in accordance with the present invention.

FIG. 5 is a fragmentary sectional view of an aphakic eye 10 having a cornea 12, iris 14, pupil 16 and line of sight 18. An intraocular lens 30 constructed in accordance with a first embodiment of the invention is mounted in the eye 10. The intraocular lens 30 has asymmetric haptics including a superior haptic 32 and an inferior haptic 34. The fixation of the haptics 32, 34 is symmetric: i.e., each haptic 32, 34 engages the same ocular structure, in this case the capsular bag 26.

Figure 6:
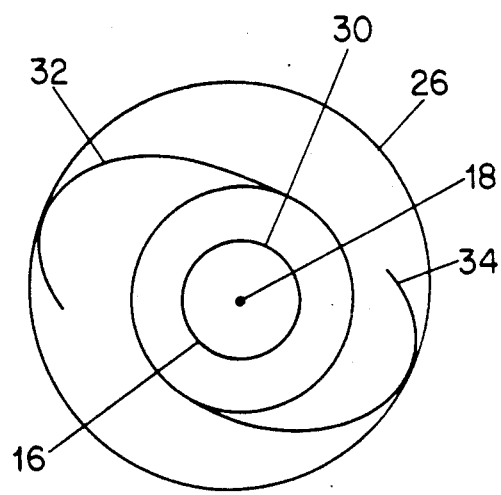
FIG. 6 is a view in front elevation of the structure of FIG. 5.

As FIG. 6 shows, the capsular bag 26 is not normally centered with respect to the line of sight 18. In the first embodiment of the invention, therefore, the haptics 32, 34 are given a compensating asymmetry, the superior haptic 32 being longer or less flexible than the inferior haptic 34 so that the center of the optical zone of the intraocular lens 30 is on the line of sight, provided only that the intraocular lens 30 is centered with respect to the pupil 16, thereby minimizing the risk of exposure of an edge of the lens 30 through the pupil 16. Further in accordance with the invention, both haptics 32, 34 are either angled or stepped as illustrated in FIG. 5 to compensate for the lens tilt that normally results even in the case of symmetric fixation of the haptics. The stepped or angular adjustment of the haptics is such as to compensate for tilt when the lens is dialed or otherwise oriented to an azimuth that compensates for decentration. Thus, compensation for decentration and tilt can be accomplished concurrently.

One preferred goal is to mount the intraocular lens so that its optical axis coincides with the visual axis of the eye and its optical zone is centered on the pupil (in other words, the center of the optical zone lies on the line of sight), thereby compensating for both decentration and tilt, while avoiding exposure of an edge of the lens through the pupil. It is also within the scope of the invention to compensate for decentration but not tilt or to compensate for tilt but not decentration. Preferably, however, in accordance with the invention compensation is made for both decentration and tilt, so that the lens is implanted in a manner that introduces neither prismatic nor cylindrical error.

Since the decentration in the right eye mirrors the decentration in the left eye and the tilt in the right eye mirrors the tilt in the left eye, an IOL constructed in accordance with the invention and intended for implantation in a right eye must be a mirror image (except for refractive prescription) of an IOL intended for implantation in a left eye.

Figure 7:
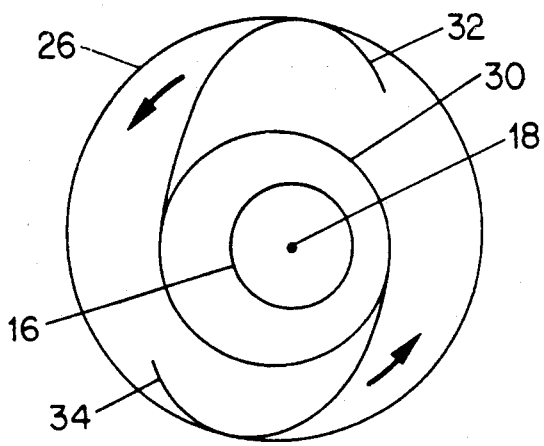
FIG. 7 is a fragmentary sectional view in front elevation of an aphakic left eye showing the insertion therein with symmetric fixation of a lens in accordance with the invention, the haptics being mounted with their long axis vertical.

FIG. 7 is a fragmentary sectional view in front elevation of an aphakic left eye showing the insertion therein with symmetric fixation of a lens in accordance with the invention, the haptics being mounted with their long axis vertical. In FIG. 7, the pupil 16 is decentered relative to the capsular bag 26. The intraocular lens 30 is mounted with the superior haptic 32 either longer or less flexible than the inferior haptic 34, and with the haptics arranged along a vertical axis as indicated in FIG. 7 the intraocular lens 30 is not centered on the pupil 16.

Figure 8:
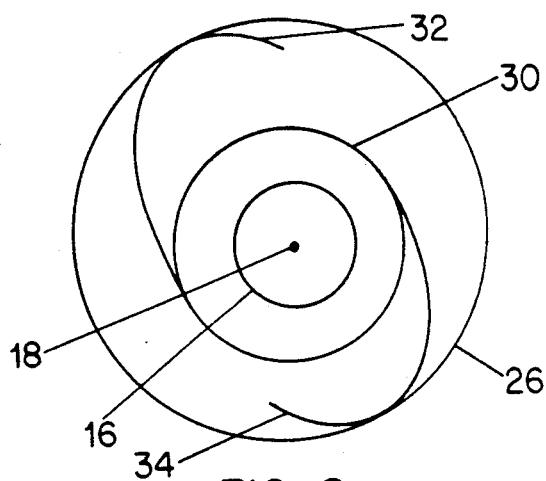
FIG. 8 is a view corresponding to FIG. 7 and showing the reorientation as by dialing of the lens substantially 45° counterclockwise to eliminate decentration.

In FIG. 8, however, the intraocular lens 30 is properly centered on the pupil 16. The intraocular lens 30 has been dialed or otherwise reoriented in FIG. 8 as compared to its orientation in FIG. 7 in a counterclockwise direction so that the intraocular lens 30 is repositioned in such a manner that its optical zone center is coincident with the line of sight 18.

Figure 9:
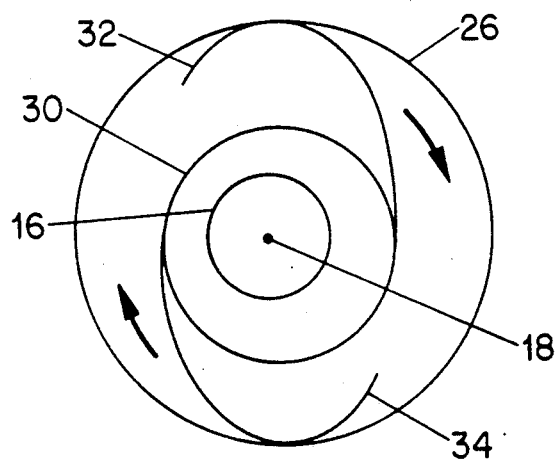
FIG. 9 is a fragmentary sectional view in front elevation of an aphakic right eye showing the insertion therein with symmetric fixation of a lens in accordance with the invention, the haptics being mounted with their long axis vertical.
Figure 10:
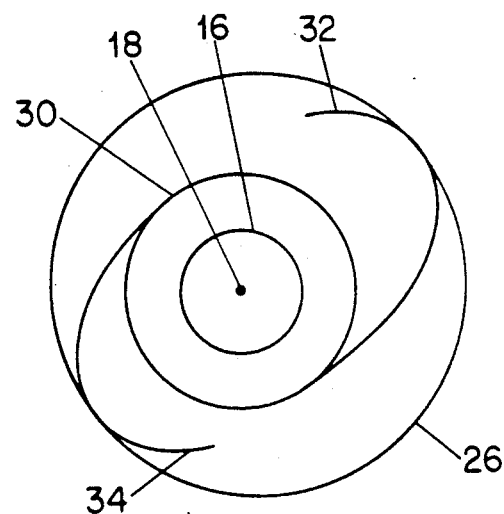
FIG. 10 is a view corresponding to FIG. 9 and showing the reorientation as by dialing of the lens substantially 45° clockwise to eliminate decentration.

The lens shown in FIGS. 7 and 8 has a refractive portion that may be radially symmetrical so that its optical center coincides with the center of optical zone, and the positioning of the lens to eliminate decentration and tilt may be done by proper design of the haptics. However, without use of a lens that is asymmetric as indicated below there is a greater risk that the intraocular lens will not fully cover the pupil. In principle, an intraocular lens having a refractive portion of symmetric design could be made large enough to cover the pupil; in practice, however, the intraocular lens optical zone diameter (6 to 7 millimeters) is normally relatively inflexible and cannot be too large to fit through the fully dilated pupil or too heavy to be supported within the eye. Moreover, it is desirable to keep the incision in the eye as small as possible, and the size of the lens is limited by the size of the acceptable incision. FIGS. 9 and 10 are respectively similar to FIGS. 7 and 8 but show a lens that is a mirror image of the intraocular lens 30. In particular the haptics of the lens in FIGS. 9 and 10 are curved in such a manner as to permit clockwise dialing as opposed to the counterclockwise dialing of which the lens of FIGS. 7 and 8 is capable. The lens of FIGS. 9 and 10 is thus adapted to be mounted in a right eye so that it can be dialed or otherwise oriented to a position (FIG. 10) wherein the optical zone of the refractive portion 30 is centered on the pupil 16.

Figure 11:
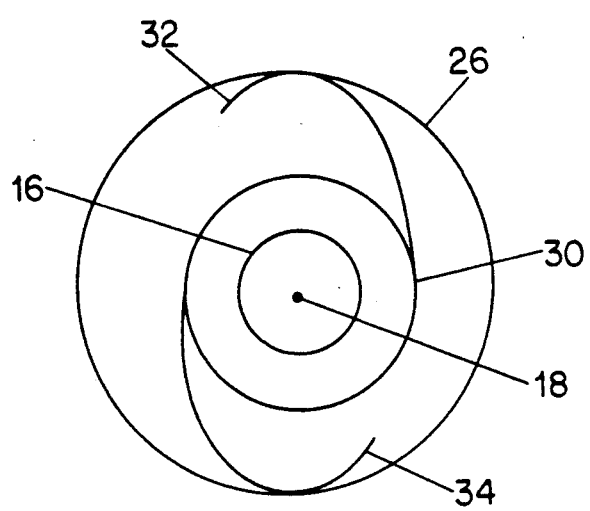
FIG. 11 is a view in front elevation showing that the refractive portion of the intraocular lens can be centered on the pupil with the haptics arranged with their long axis extending along any azimuth preferred by the surgeon, for example with the haptic axis extending in a vertical direction.

FIG. 11 shows that the refractive portion of the intraocular lens can be centered in the pupil with the haptics arranged along a vertical axis, for example. This is the orientation preferred by many surgeons. Clearly, any azimuth can be selected for the long axis of the haptics in accordance with the present invention.

Figure 12:
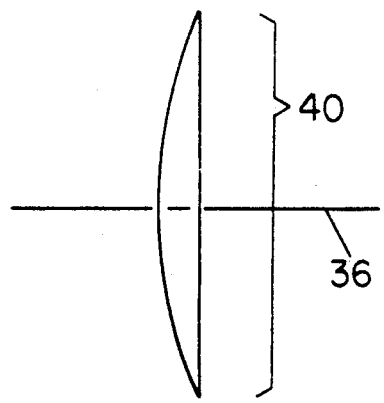
FIG. 12 is a sectional view of a radially symmetric intraocular lens in a plane containing the optical axis of the lens.

FIG. 12 is a sectional view of a refractive portion of a radially symmetric intraocular lens in a plane containing the optical axis 36 of the lens. Such a refractive portion can be used in the lens of FIGS. 7 and 8 or FIGS. 9 and 10. In FIG. 12 the center of the optical zone 40 lies on the optical axis 36.

Figure 13:
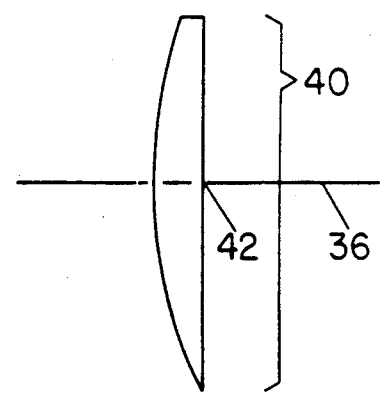
FIG. 13 is a sectional view of another embodiment of an intraocular lens constructed in accordance with the present invention in a plane containing the optical axis and the center of the optical zone of the lens.

FIG. 13 shows a preferred embodiment of the invention wherein the optical axis 36 is displaced from the center of the optical zone 40. In accordance with the invention, the optical axis 36 either intersects the visual axis of the eye at the optical center 42 or is parallel to the visual axis of the eye. Preferably, the optical axis 36 of the lens is coincident with the visual axis of the eye.

Figure 14:
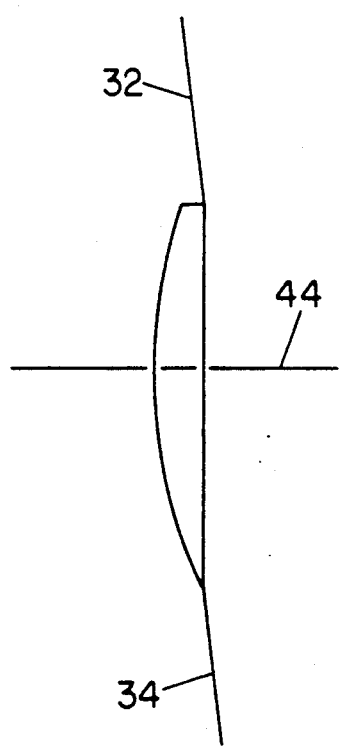
FIG. 14 is a view corresponding to FIG. 13 and showing the addition of haptics in accordance with the invention.

FIG. 14 shows the lens of FIG. 13 with the addition of haptics. The haptics are angled as indicated or alternatively stepped and/or are of unequal length so that they compensate not only for decentration but also for tilt. In addition to the compensation clearly visible in FIG. 14, it is possible to introduce a relative twisting of the refractive portion of the lens relative to the haptics, whereby, regardless of the optical structure engaged by the haptics and regardless of the azimuth of the haptic axis, the tilt of the refractive portion of the lens can be compensated.

Figure 15:
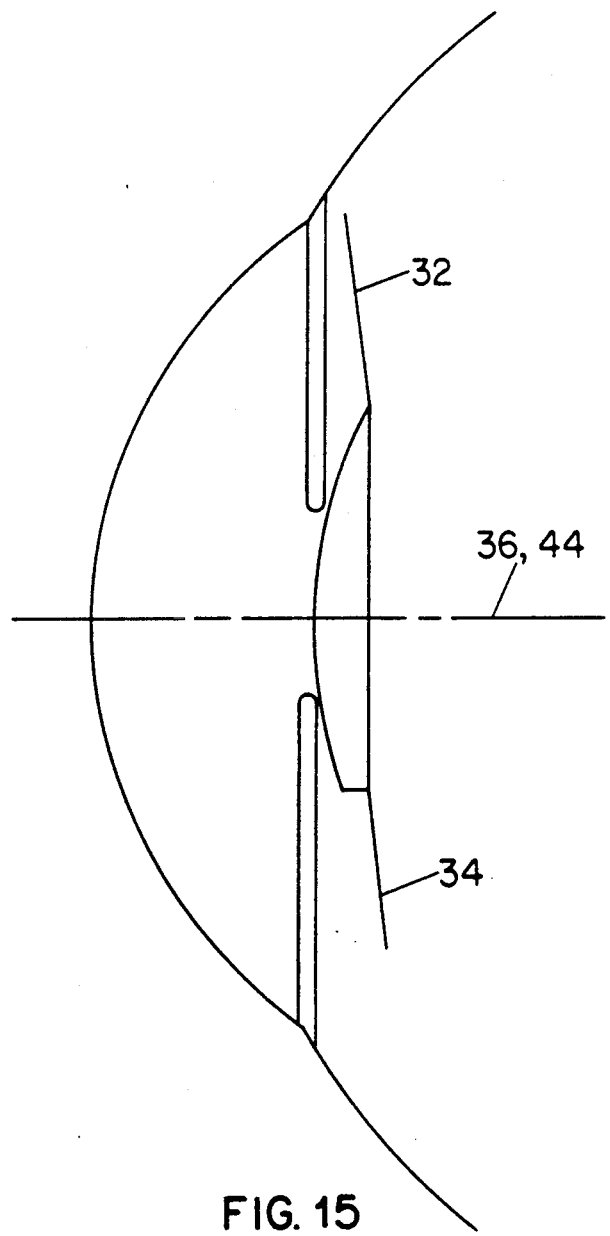
FIG. 15 is a sectional view in a vertical plane containing the optical/visual axis and showing the lens of FIG. 12 mounted in an aphakic eye.

FIG. 15 shows the lens of FIG. 14 mounted in an aphakic eye. The visual axis 44 of the eye coincides with the optical axis 36 shown in FIG. 13. Thus both decentration and tilt are compensated at the same time, and the optical zone is centered on the pupil, whereby the risk of exposure of an edge of the intraocular lens through the pupil is minimized. The construction of the haptics will depend on the ocular structure engaged by the haptics and the azimuth of the long axis of the haptics as measured in the eye. In general, the haptics can be asymmetric to the extent necessary to position the refractive portion of the intraocular lens in accordance with the principles of the present invention.

Figure 16:
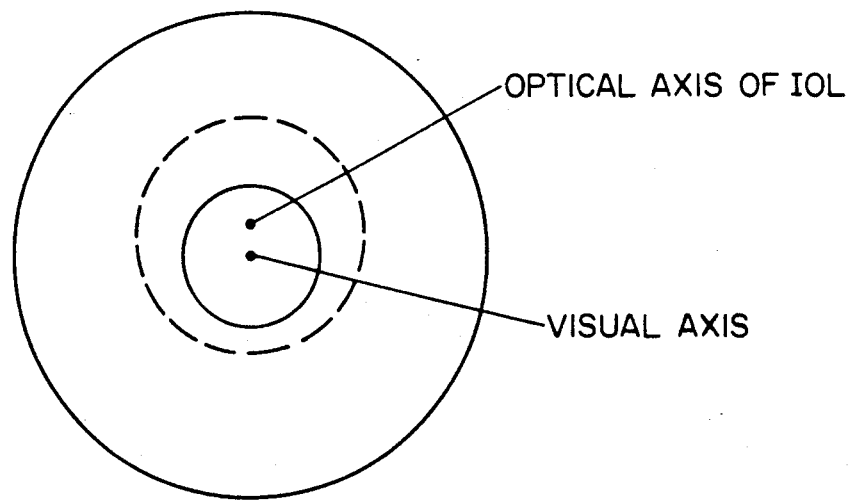
FIG. 16 is a view in front elevation of an IOL decentered in such a way that the optical axis of the lens and the visual axis of the eye are parallel to each other and are spaced by a predetermined distance.
Figure 17:
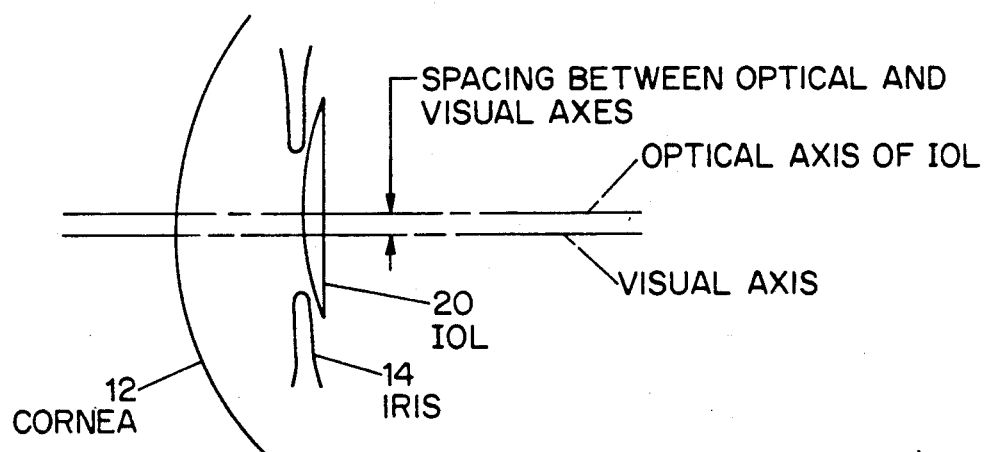
FIG. 17 is a fragmentary sectional view of the structure of FIG. 16.

FIGS. 16 and 17 show an IOL decentered in such a way that the optical axis of the lens and the visual axis of the eye are parallel to each other and are spaced by a predetermined distance.

Figure 18:
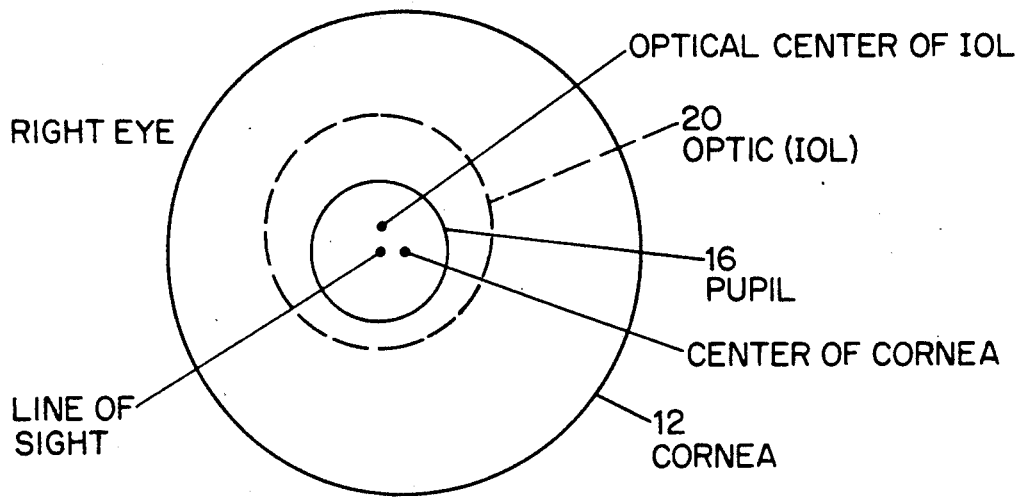
FIG. 18 is a view in front elevation of an IOL located such that the optical center of the lens is decentered superotemporally.

FIG. 18 illustrates an IOL location such that the optical center of the lens is decentered superotemporally, so that the prism effect induced by the IOL matches in magnitude and direction that induced by the crystalline lens.

It has been found that IOLs are decentered more in eyes with greater axial length, while they tend to be tilted more in eyes with shorter axial length. Axial length is usually measured pre-operatively to help determine the correct power for the IOL. In cases where the axial length is unusually long or short, the IOL could be designed to compensate tilt and decentration by the appropriate amount.

Similarly, it may be desired to measure the tilt and decentration of the natural lens before surgery. This can be done optically if the cataract does not obscure the image reflected from the posterior surface. Otherwise, ultrasound may be employed. If the measurements on a particular patient indicate the need, an IOL designed to compensate for the expected tilt and decentration of the lens in this patient can be implanted.

Thus there is provided in accordance with the invention a novel and highly effective intraocular lens and method of restoring substantially normal vision to an aphakic eye. Certain bifocal and multifocal IOLs may be more sensitive to decentration and/or tilt than are conventional IOLs, and therefore would particularly benefit from the invention.

Many modifications of the preferred embodiments of the invention disclosed herein will readily occur to those skilled in the art. For example, the present invention is applicable to mounting in the anterior or posterior chamber, to lenses in which three or more haptics are employed, and to lenses wherein the haptics engage any ocular structure. Moreover, the invention is in no way limited to the materials employed to make the lens. Similarly, the method of the invention is applicable to mounting of the intraocular lens in either the anterior or posterior chamber, to orientation of the haptics along any azimuth, and to engagement of the haptics with any ocular structure.

Accordingly, the invention is to be construed as including all methods and structure that fall within the scope of the appended claims.

What is claimed is:

1. An intraocular lens for mounting in an aphakic eye, the lens having refractive means defining an optical zone and haptic means extending out from the refractive means, the refractive means and haptic means having a combined structure that exhibits handedness, whereby, when the haptic means engages the eye in a predetermined manner, ocular characteristics that affect the position of the lens in the eye and that are statistically different in the case of implantation in right and left eyes, respectively, are compensated for so that the optical zone is centered on the pupil.

2. An intraocular lens for mounting in an aphakic eye having a line of sight, the intraocular lens having refractive means defining an optical zone and haptic means extending out from the refractive means, the refractive means and haptic means forming a combined structure that exhibits handedness, whereby, when the haptic means engages the eye in a predetermined manner, ocular characteristics that affect the tilt of the lens in the eye and that are statistically different in the case of implantation in right and left eyes, respectively, are compensated for so that the tilt of the lens can be made to assume any predetermined value relative to the line of sight.

3. An intraocular lens according to claim 2, wherein said tilt is such as to introduce substantially no astigmatism.

4. An intraocular lens according to claim 2, wherein said tilt is such as to introduce a non-zero astigmatism.

5. An intraocular lens for mounting at a given lens mounting location in an aphakic eye having a pupil, a line of sight and a visual axis which at a given lens mounting location in the eye is displaced from the line of sight by a given distance, the lens comprising (i) refractive means having an optical axis, an optical center, and optical zone and an optical zone center displaced from the optical center by a distance having a predetermined relation to said given distance and (ii) haptic means extending out from the refractive means and being so related to the refractive means that when the haptic means engages the eye in a predetermined manner at said given lens mounting location ocular characteristics that affect the position of the lens in the eye and that are statistically different in the case of implantation in right and left eyes are at least partially compensated for so that the optical zone is centered on the pupil and the optical and visual axes have a prescribed relation with respect to each other.

6. An intraocular lens for placement in an aphakic eye having a pupil and a visual axis, the lens being formed with refractive means defining an optical axis, an optical center, and an optical zone and with haptic means extending out from the refractive means for positioning the lens in the eye, the refractive means and the haptic means being formed relative to each other so that the lens can be mounted in the eye with a predetermined azimuth ocular characteristics that affect the position of the lens in the eye and that are statistically different in the case of implantation in right and left eyes are at least partially compensated for such that the optical zone is centered on the pupil and the optical and visual axes have a prescribed relation with respect to each other.

7. An intraocular lens according to either of claims 5 or 6 wherein said prescribed relation is such that the optical and visual axes are coincident.

8. An intraocular lens according to either of claims 5 or 6 wherein said prescribed relation is such that the optical center lies in the visual axis.

9. An intraocular lens according to either of claims 5 or 6 wherein said prescribed relation is such that the optical and visual axes are parallel and spaced apart from each other.

10. An intraocular lens according to either of claims 5 or 6 wherein said prescribed relation is such as to reproduce a naturally occurring prism of a crystalline lens.

11. An intraocular lens exhibiting handedness and comprising refractive means and haptic means extending out from the refractive means, the lens being designed to compensate for ocular characteristics that affect centration or tilt and that are statistically different in the case of implantation in right and left eyes, respectively, the intraocular lens being radially asymmetric in such a manner that, except for structural characteristics attributable to refractive prescription, a lens intended for implantation in a left eye is a mirror image of a lens intended for implantation in a right eye, whereby, when the haptic means engages the eye in a predetermined manner, ocular characteristics that affect centration or tilt and that are statistically different in the case of implantation in right and left eyes, respectively, are at least partially compensated for with respect to decantration and tilt in relation to the pupil or line of sight.

12. A method of improving vision of an aphakic eye having a pupil, a line of sight and a measurement axis which at a given lens mounting location in the eye is displaced from the line of sight by a given distance, the method comprising the steps of mounting at said mounting location an intraocular lens formed with (i) refractive means having an optical axis, an optical center, an optical zone and an optical zone center displaced from the optical center by a distance having a predetermined relation to said given distance and (ii) haptic means extending out from the refractive means and forming a combined structure that exhibits handedness and being so related to the refractive means that, when the haptic means engages the eye in a predetemined manner for mounting the lens at said given lens mounting location, ocular characteristics that affect the position of the lens in the eye and that are statistically different in the case of implantation in right and left eyes are at least partially compensated for so that the opical and measurement axes have a prescribed relation with respect to each other and the optical zone is centered on the pupil.

13. A method according ot claim 12 wherein said prescribed relation is such that the optical and measurement axes are coincident.

14. A method according to claim 12 wherein said prescribed relation is such that the optical center lies in the measurement axis or line of sight.

15. A method according to claim 12 wherein said prescribed relation is such that the optical and measurement axes are parallel and spaced apart from each other.

16. A method according to claim 12 wherein said prescribed relation is such as to reproduce a naturally occurring prism of a crystalline lens.

17. A method of improving vision of an aphakic eye, the eye having a pupil and the method comprising the steps of inserting in the eye an intraocular lens formed with refractive means of a suitable dioptic power and having an optical axis, an optical axis, an optical zone center, and a pair of asymmetric haptics and forming a combined structure that exhibits handedness, the optical axis being displaced from the optical zone center and the haptics being arranged along a haptic axis, and enging the haptics with the same ocular structure, thereby establishing symmetric haptic fixation, the haptic axis being oriented so that ocular characteristics that affect the position or tilt of the lens in the eye and which are statistically different in the case of implantation in right and left eyes are at least partially compensated for so that the optical zone is substantially centered on he pupil and the displacement and orientation of the optical axis and the optical zone center relative to each other compensates for at least one of (i) decentration and (ii) tilt induced along any predetermined meridian relative to the haptic axis.

18. A method of implanting, in an aphakic eye having a visual axis and a pupil having a center displaced from the visual axis, an intraocular lens having haptic means, an optical axis, an optical center and an optical zone and forming a combined structure that exhibits handedness, the method comprising the steps of orienting the intraocular lens to a predetermined azimuth and engaging the haptic means with predetermined ocular structure, so that ocular characteristics that affect the position and tilt of the lens in the eye and which are statistically different in the case of implantation in right and left eyes are at least partially compensated for an dso that the visual axis is parallel to the optical axis or intersecting the optical center and the optical zone being concentric with the pupil.

19. A method of implanting, ain an aphakic eye having a visual axis and a pupil having a center displaced from the visual axis, an intraocular lens having haptic means and an optical axis and forming a combined structure that exhibits handedness, the method comprising the steps of engaging the haptic means with predetermined ocular structure, so that ocular characteristics that affect the tilt of the lens in the eye and which are statistically different in the case of implantation in right and left eyes are at least partially compensated for and so that the haptic means is oriented along an azimuth such that the optical axis is coincident with the visual axis.

* * * * *